(12) United States Patent
Yaremchuk

(10) Patent No.: US 9,913,704 B1
(45) Date of Patent: Mar. 13, 2018

(54) CRANIOFACIAL SURGERY IMPLANT SYSTEMS AND METHODS

(75) Inventor: Michael J. Yaremchuk, Lynnfield, MA (US)

(73) Assignee: Michael J. Yaremchuk, Lynnfield, MA (US)

( * ) Notice: Subject to any disclaimer, the term of this patent is extended or adjusted under 35 U.S.C. 154(b) by 1847 days.

(21) Appl. No.: 12/342,762

(22) Filed: Dec. 23, 2008

Related U.S. Application Data

(60) Provisional application No. 61/018,943, filed on Jan. 4, 2008, provisional application No. 61/018,948, filed on Jan. 4, 2008, provisional application No. 61/018,952, filed on Jan. 4, 2008.

(51) Int. Cl.
*A61F 2/02* (2006.01)

(52) U.S. Cl.
CPC ..................... *A61F 2/02* (2013.01)

(58) Field of Classification Search
CPC ........................................... A61F 2/02
USPC .......................... 623/17.18, 17.19
See application file for complete search history.

(56) References Cited

U.S. PATENT DOCUMENTS

| | | |
|---|---|---|
| 717,526 A | 1/1908 | Barney |
| 1,920,821 A | 8/1933 | Wassenaar |
| 2,665,692 A | 1/1954 | L'Esperance |
| 4,610,252 A | 9/1986 | Catalano |
| 4,764,168 A | 8/1988 | Suh |
| 4,803,983 A | 2/1989 | Siegel |
| 4,959,065 A | 9/1990 | Arnett et al. |
| 5,195,951 A | 3/1993 | Giampapa |
| 5,320,637 A | 6/1994 | Borders, Jr. |
| 5,380,329 A * | 1/1995 | Elia .................. A61B 17/58 606/330 |
| 5,391,181 A | 2/1995 | Johnson et al. |
| 5,421,831 A | 6/1995 | Giampapa |
| 5,496,371 A | 3/1996 | Eppley et al. |
| 5,514,179 A | 5/1996 | Brennan |
| 5,554,194 A | 9/1996 | Sanders |
| 5,578,032 A | 11/1996 | Lalonde |
| 5,643,316 A | 7/1997 | Kaiser et al. |
| 5,658,516 A | 8/1997 | Eppley et al. |
| 5,971,775 A | 10/1999 | Tor et al. |
| RE37,249 E | 6/2001 | Leibinger et al. |
| 6,277,150 B1 | 8/2001 | Crawley et al. |
| 6,302,884 B1 | 10/2001 | Wellisz et al. |
| 6,551,608 B2 | 4/2003 | Yao |
| 6,582,435 B2 | 6/2003 | Wellisz et al. |
| D488,229 S | 4/2004 | Rinner et al. |
| 7,008,455 B2 | 3/2006 | Raphael et al. |
| 7,104,475 B2 | 3/2006 | Mongold |
| 7,066,962 B2 | 6/2006 | Swords |
| D540,264 S | 4/2007 | Zhang |

(Continued)

FOREIGN PATENT DOCUMENTS

RU     2074672 C1     3/1997

OTHER PUBLICATIONS

English Abstract, RU 2074672 C1, Beletskij Boris Ivanovich et al., Mar. 10, 1997.

(Continued)

*Primary Examiner* — Matthew Schall
(74) *Attorney, Agent, or Firm* — Goodwin Procter LLP

(57) ABSTRACT

Various embodiments of craniofacial implants, surgical instruments, and techniques are described to provide improved surgical results.

17 Claims, 16 Drawing Sheets

(56) References Cited

U.S. PATENT DOCUMENTS

| | | |
|---|---|---|
| D606,496 S | 12/2009 | Ngo |
| D608,293 S | 1/2010 | Ngo |
| D610,548 S | 2/2010 | Ngo |
| D621,364 S | 8/2010 | Kasahara |
| D623,138 S | 9/2010 | Ngo |
| 2003/0224654 A1 | 12/2003 | Wu |
| 2004/0138591 A1 | 7/2004 | Iseki et al. |
| 2005/0085850 A1 | 4/2005 | Harris, Jr. et al. |
| 2006/0116682 A1 | 6/2006 | Longo |
| 2006/0217813 A1 | 9/2006 | Posnick et al. |
| 2006/0224242 A1* | 10/2006 | Swords et al. ............. 623/17.19 |
| 2007/0067041 A1 | 3/2007 | Kotoske |
| 2007/0156171 A1 | 7/2007 | Lang et al. |
| 2010/0112834 A1 | 5/2010 | Chen et al. |
| 2010/0184339 A1 | 7/2010 | Ngo et al. |

OTHER PUBLICATIONS

Ramirez, "Mandibular Matrix Implant System: A Method to Restore Skeletal Support to the Lower Face," Jul. 2000, vol. 106(1), pp. 176-189.

Yaremchuk, "Atlas of Facial Implants", Elsevier, © 2007, 244 pages.

\* cited by examiner

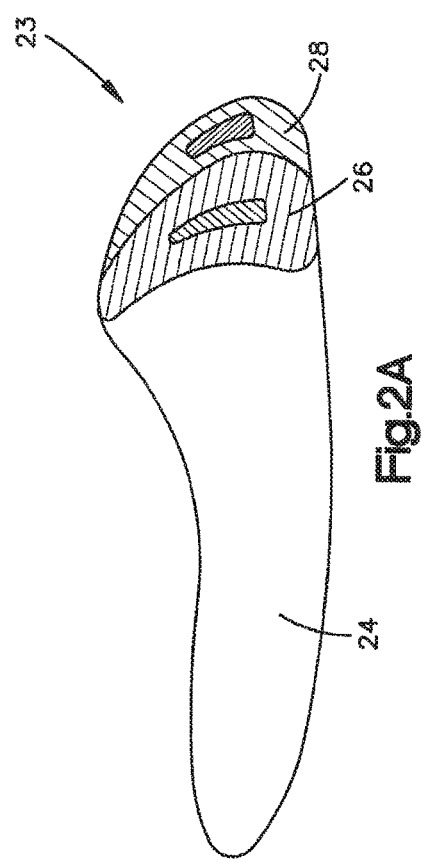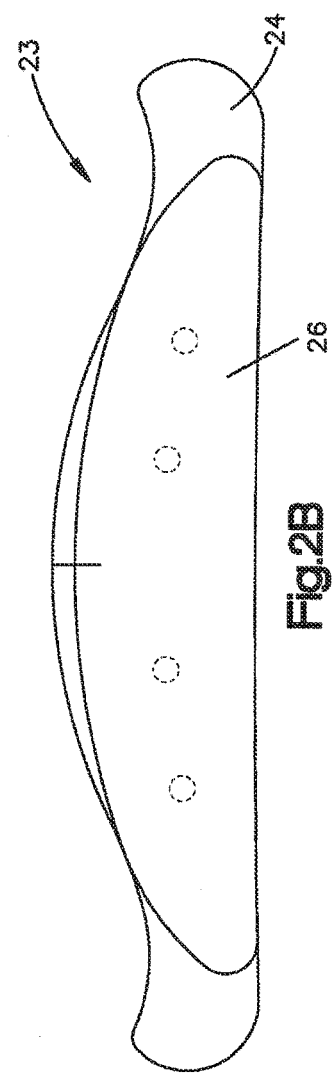
Fig.2A
Fig.2B

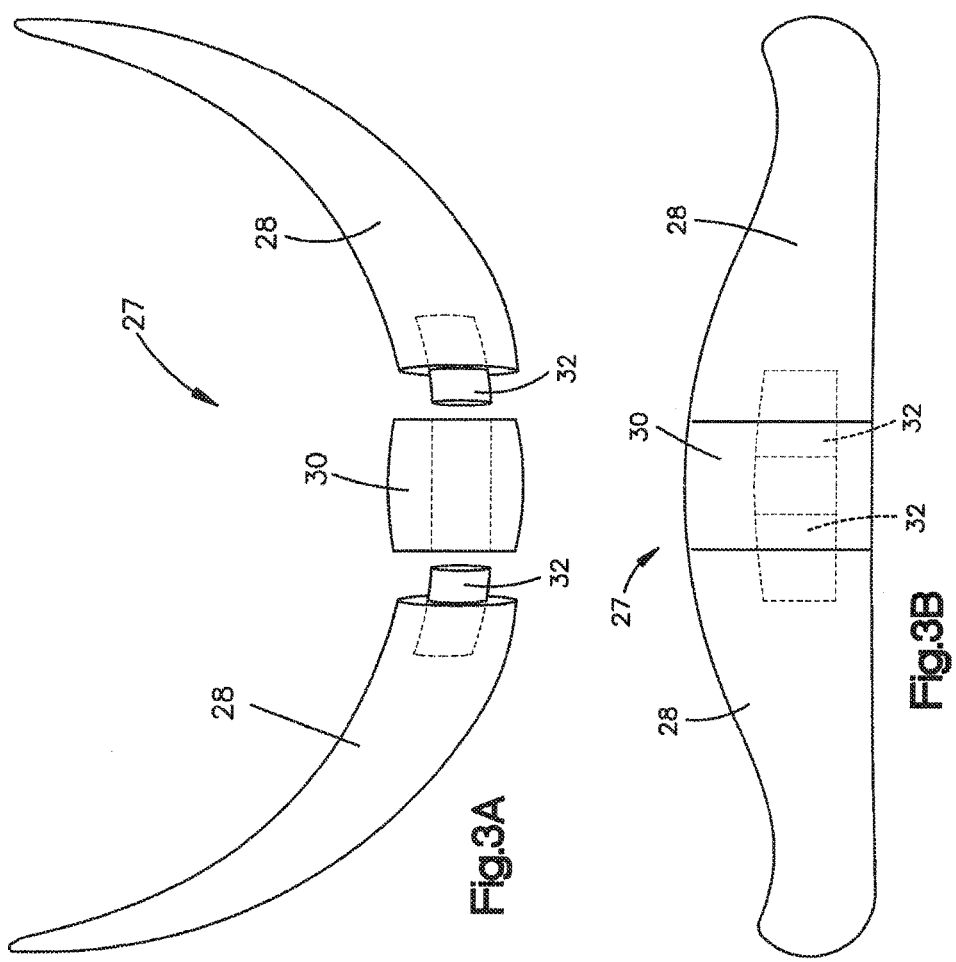

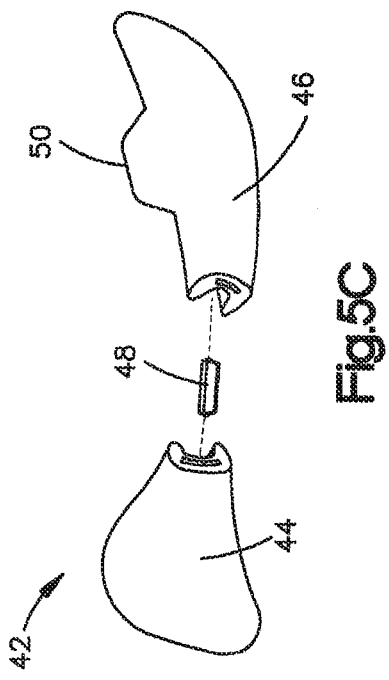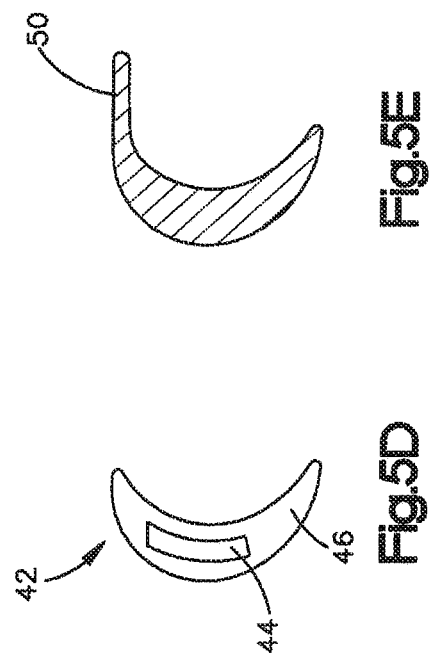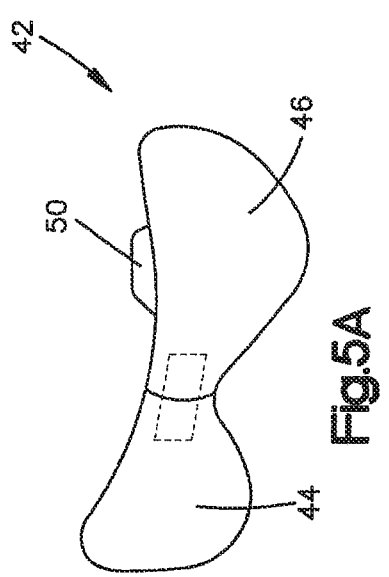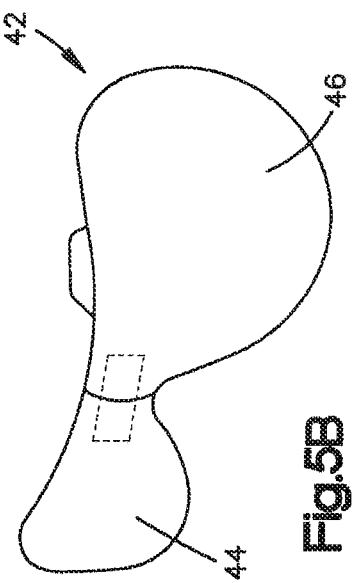

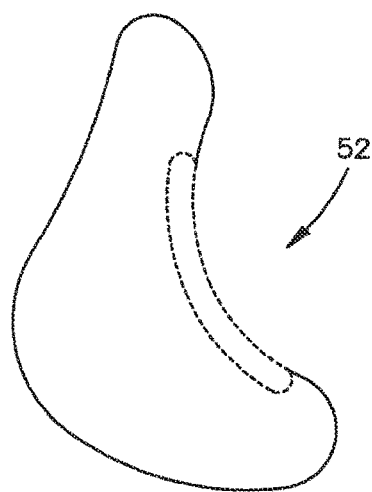 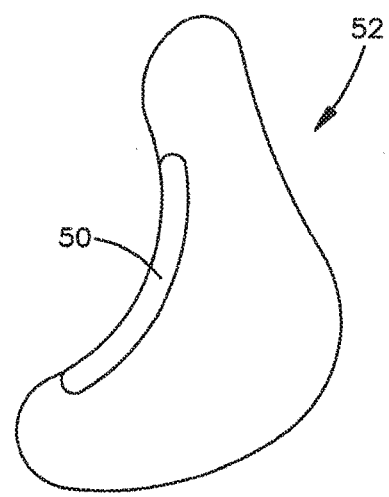
Fig.8A  Fig.8B
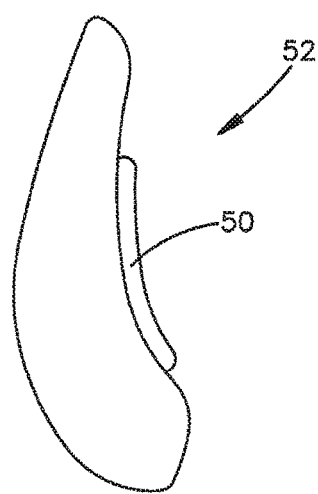
Fig.8C

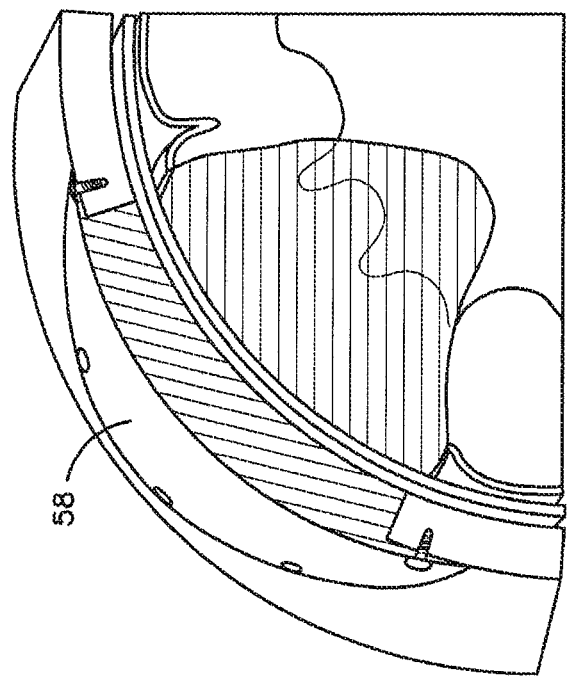
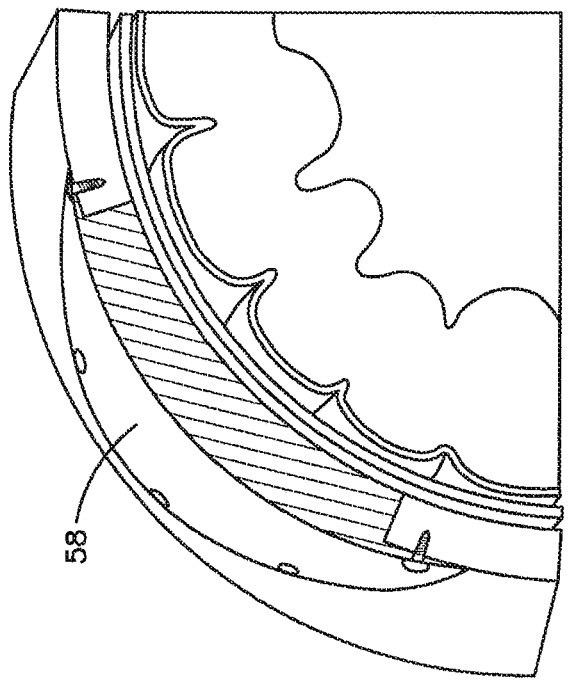

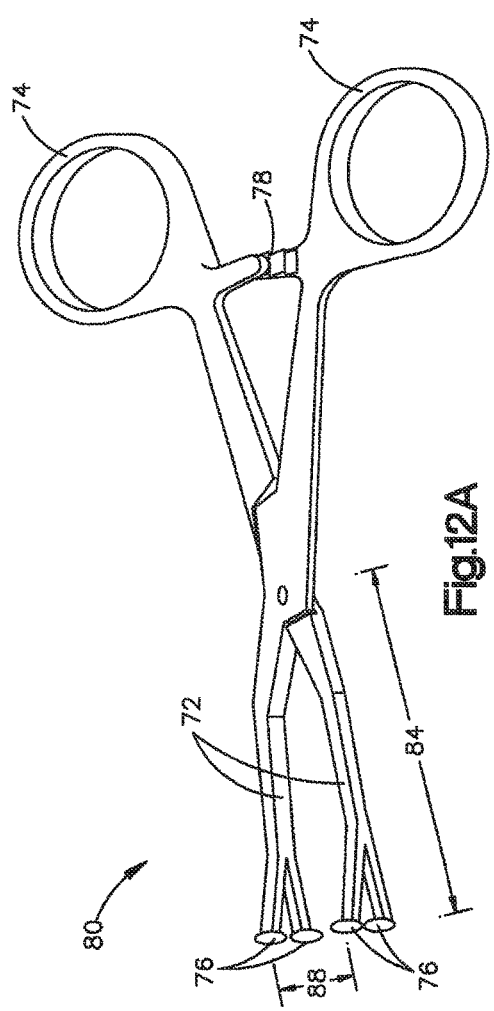
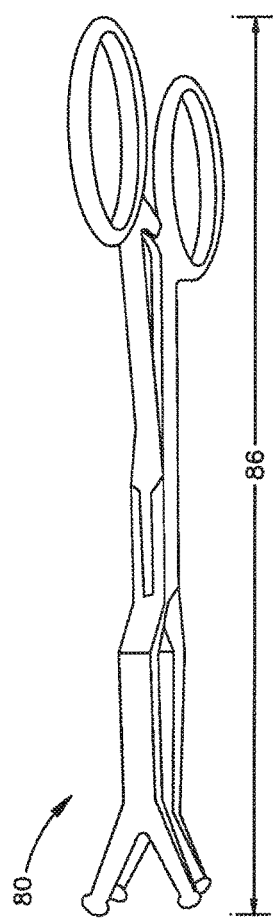
Fig.12A
Fig.12B

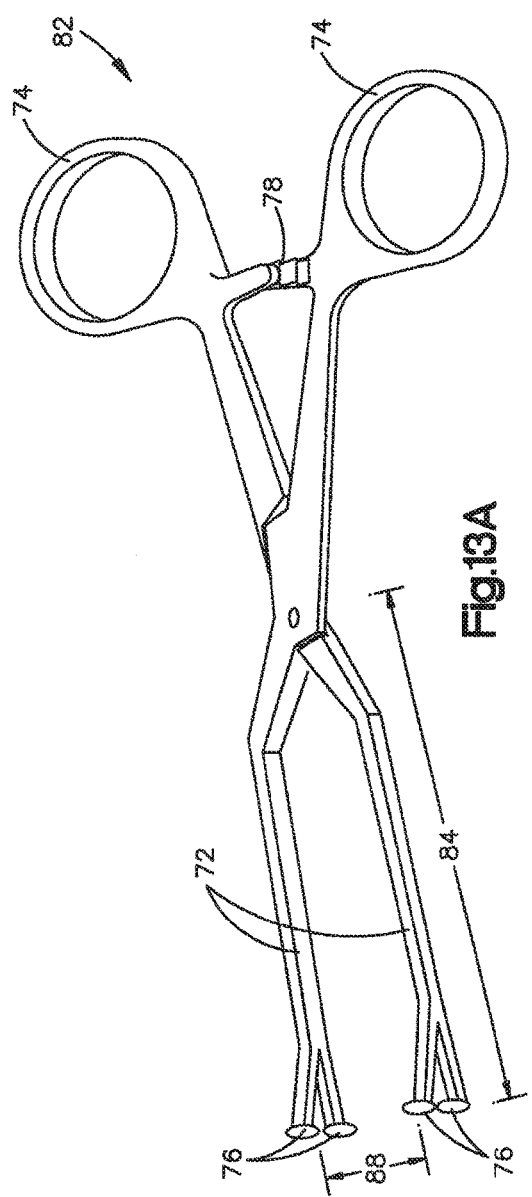
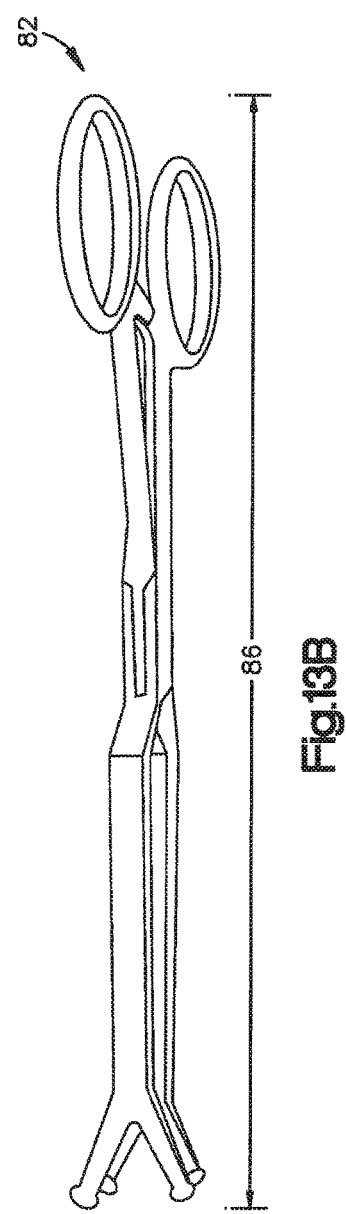
Fig.13A
Fig.13B

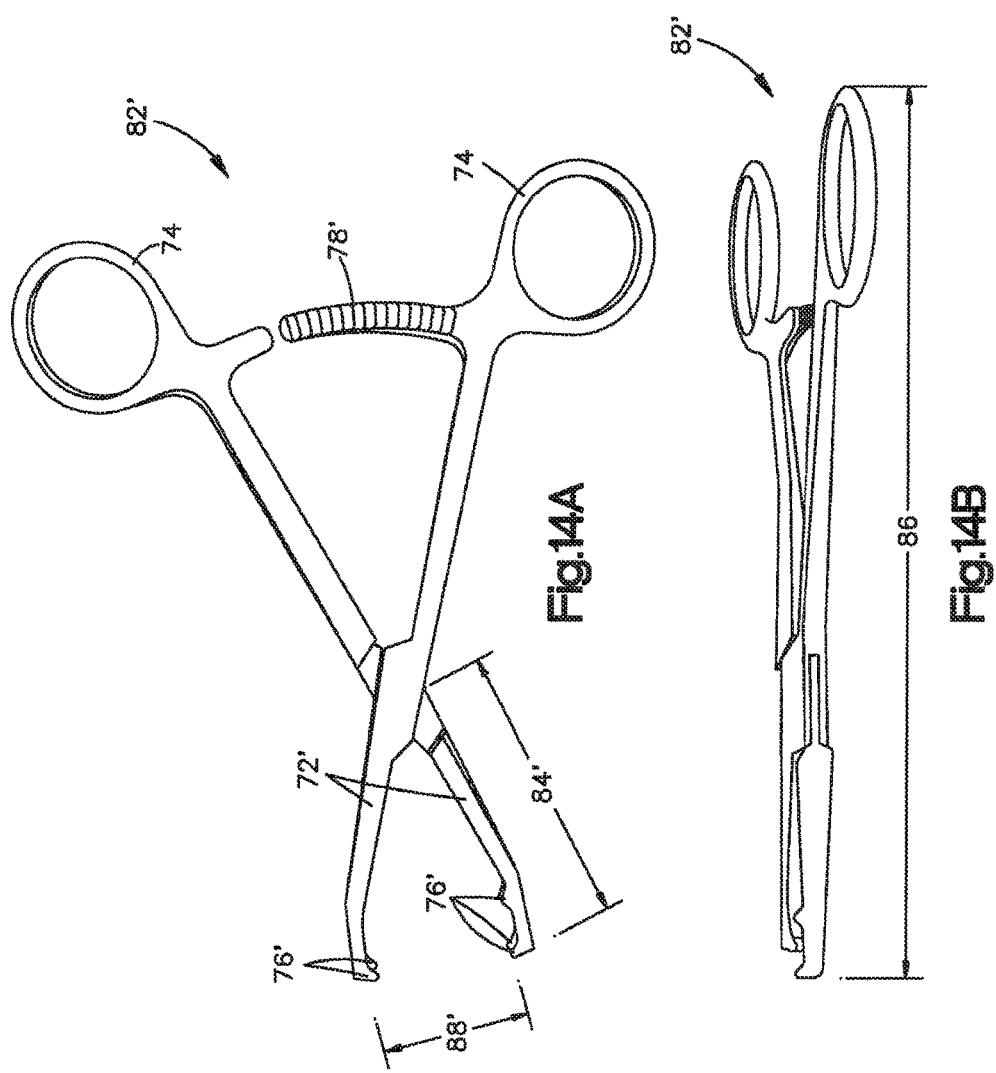

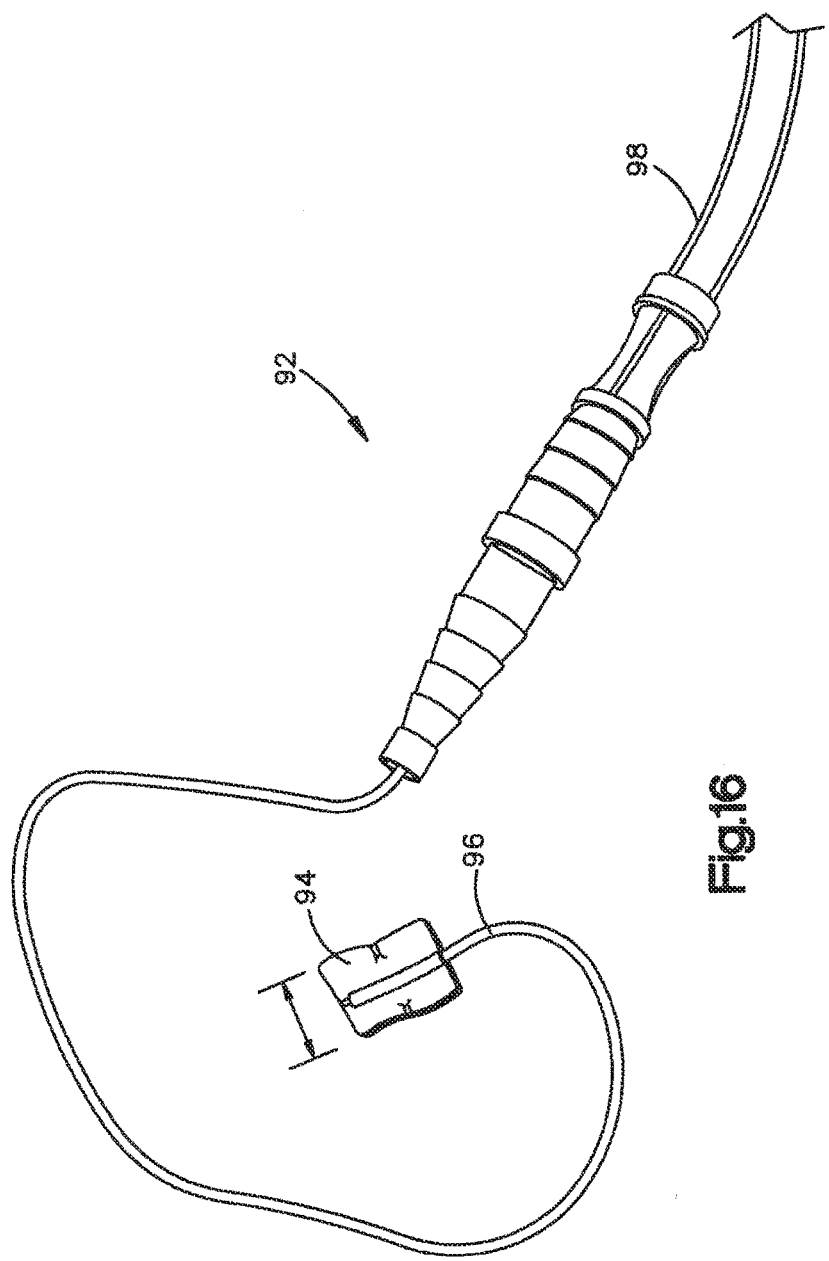

CRANIOFACIAL SURGERY IMPLANT SYSTEMS AND METHODS

CROSS-REFERENCE TO RELATED APPLICATIONS

This application claims priority to and incorporates by reference the entire disclosure of each of the following three provisional U.S. patent applications: U.S. Ser. No. 61/018,943 filed Jan. 4, 2008, titled "Multi-Component Craniofacial Surgery Implant Systems and Methods"; U.S. Ser. No. 61/018,948 filed Jan. 4, 2008, titled "Craniofacial Implant Registration Features and Methods"; and U.S. Ser. No. 61/018,952 filed Jan. 4, 2008, titled "Craniofacial Implant Surgical Instruments and Methods."

FIELD OF THE INVENTION

The invention relates to surgical implants and more specifically to craniofacial implant systems and associated surgical methods employing multiple mating components and registration features on the implants. The invention further relates to surgical instruments and more specifically to craniofacial implant surgical instruments and associated surgical methods.

BACKGROUND OF THE INVENTION

Craniofacial surgery is generally performed to treat congenital deformities of the face and facial skeleton, to treat traumatic injury, or to address cosmetic or aesthetic concerns of the patient. Skilled surgeons can enhance or reconstruct the facial skeleton using biocompatible implants that are disposed beneath the facial musculature and applied to or attached to the facial skeleton (typically using screw fasteners). For example, craniofacial surgery and biomaterials can be used to create new facial skeletal contours. See, for example, ATLAS OF FACIAL IMPLANTS (Elsevier, 2007) by Michael J. Yaremchuk, MD, the disclosure of which is incorporated herein by reference in its entirety. Unlike the use of injected liquid materials, that are meant to inflate the soft tissue envelope, the use of solid facial implants can mimic the facial appearance obtained with more extensive facial skeletal surgeries that require cutting and repositioning of facial bone. The facial implants are typically provided in a limited number of basic shapes, that can be carved and shaped by the surgeon at the time of implant.

Facial implants are conventionally made from silicone rubber or sintered porous plastics (such as polyethylene) that are molded into predetermined shapes, depending on the area of the face to be treated. See, for example, U.S. Pat. No. 6,551,608, the disclosure of which is incorporated herein by reference in its entirety. For each area, a family of implants of varying size and similar contour are often provided. This is required, so that the facial implants can be readily customized to suit both the underlying skeletal contours and the overlying facial tissue, in order to give the desired final appearance, without excessive sculpting of the implant by the surgeon during the implant procedure.

Problems can exist, however, due to the relatively large size of some of the implants (e.g., requiring more extensive surgical access to the area to be augmented) and/or the amount of customization and associated time required, due to the limited selection of implants in each family. In general, temporary size implants are often used intraoperatively to determine which implant shape might be appropriate, which requires a large inventory of implants to be available to the surgeon. Implants which are not optimal for the specific needs of the patient can sometime be used. Implants of different sizes must be custom carved and, in extreme cases, stacked and joined together by sutures if standard implants are not ideal for specific clinical situations. Alternatively, a shim can be custom cut and inserted underneath the implant and affixed thereto by protuberances and adhesive, as described in U.S. Pat. No. 5,514,179, the disclosure of which is incorporated herein by reference in its entirely. Current techniques can be inefficient and imprecise, and intraoperative constructs might be unstable in shape, leading to unpredictable outcomes. Further, the outcome can be less than ideal when the surgeon commits to opening an implant that, after placement, is less than ideal in projection.

The precise positioning of facial implants by the surgeon during the implant procedure is often difficult and time consuming, due to limited exposure of the areas to be augmented. Craniofacial implants are typically placed through remote access incisions to avoid visible scarring on the overlying soft tissue envelope and creation of suture lines directly over the implant which can predispose to wound breakdown, implant exposure and hence, surgical failure. Accurate implant placement is especially difficult when attempting to place a pair of implants symmetrically. For example, symmetric placement of facial implants can be problematic due to the complex three-dimension surface of the facial skeleton and limited surgical exposure.

In addition, placement of facial implants requires exposure (i.e., removal of overlying attached soft tissues) of the skeletal area to be augmented. Further, the implant needs to be held in proper position while it is being secured to the underlying bone, typically with screws. Available conventional clamps (e.g., tissue forceps, bone reduction forceps, towel clips, etc.) do not provide stable purchase of the implant and bone, due to their purchase end design, the dimensions of the purchasing end, and the configuration and orientation of the purchasing end. Inadvertent movement of the implant while it is being secured can result in implant malposition and, if recognized intraoperatively, the need to remove and reposition the implant.

SUMMARY OF THE INVENTION

In one aspect, the present invention relates to craniofacial implants including a base implant and an optional onlay component that is contoured to the surface of the base implant allowing the overall projection of the implant to be adjustable.

In one embodiment, the craniofacial implant includes a base implant having an inner contoured surface adapted to conform to a boney structure and an outer contoured surface adapted to underlie soft tissue. The craniofacial implant also includes an optional onlay component having an inner contoured surface adapted to conform to at least a portion of the outer contoured surface of the base implant and an outer contoured surface adapted to underlie soft tissue, to adjust an overall projection of the implant. The craniofacial implant may include a means to attach the onlay component to the base implant. The means to attach the onlay component to the base implant can be a press fit, connecting tabs, a locking mechanism, or a registration feature. The base block and onlay component can include a biocompatible alloplastic material.

In another aspect, the invention relates to a craniofacial implant that includes a pair of substantially mirror image implant components and an optional central segment to adjust the overall dimension of the implant. The craniofacial implant can include a pair of substantially mirror image implant components and an optional central segment adapted to be disposed therebetween and connected thereto, where the optional central segment can be selected from a group of segments having different dimensions in order to adjust the overall dimension of the implant. The craniofacial implant can include a means to attach the central segment to the implant components. The means to attach the central segment to the implant components can be a removable bar.

In another aspect, the invention relates to an adjustable elongation block implant including a base implant block having a substantially planar surface to conform to a surgically cut boney structure and an outer substantially planar opposed surface adapted to conform to an optional onlay block component and a mating surgically cut boney structure. The adjustable elongation block also includes an optional onlay block component having an inner substantially planar surface adapted to conform to the outer surface of the base implant block and an outer substantially planar opposed surface adapted to conform to at least one of an optional second onlay block component and a surgically cut boney structure, to fill a void formed by an osteotomy. The base block can be up to about 5 mm in height. The onlay component can be up to about 3 mm in height.

According to another aspect, the present invention relates to an infraorbital rim implant including a medial rim implant portion and a lateral malar implant portion that is selected from a group of at least two malar implants having at least one different dimension, to adjust an overall dimension of the implant. The infraorbital rim implant can include a means to attach the medial rim implant portion to the selected lateral malar implant portion. The means to attach the medial rim implant portion to the selected lateral malar implant portion can be a connecting extension bar. The infraorbital rim implant can be provided in a kit including a medial rim implant portion, at least two lateral malar implant portions having at least one different dimension, and a connecting extension bar.

In another aspect, the invention relates to craniofacial implants including an inner contoured surface adapted to conform to boney structure and an outer contoured surface adapted to underlie soft tissue, and a flange disposed along and extending from at least a portion of an edge thereof. The flange is adapted to abut a landmark feature of the boney structure, to position initially the implant along at least one dimension. The craniofacial implant can be selected from the group consisting of infraorbital rim implants, mandible implants, and paranasal implants. The flange can be positioned to abut the landmark feature selected from the group consisting of a lateral aspect of an orbital floor, an inferior border of a mandible body, a posterior border of a mandible ramus, and a pyriform aperture.

Another aspect of the invention relates to a horizontal osteotomy implant including a flat surface adapted to lay on an anterior face of each of a pair of relatively repositioned bones and a positioning ledge adapted to wrap around an inferior border of each of these bones.

Yet another aspect of the invention relates to a cranial implant comprising a cranial body portion adapted to substantially fill a cranial defect and a cranial thin edge portion of a periphery thereof that is adapted to receive fasteners to attach the implant to the cranium. The thin edge portion can include a taper. The taper can be from about 1.5 mm to less that 1 mm. The cranial implant may further include an intracranial inner cup having a convex surface adapted to a brain and an edge portion along at least a portion of a periphery thereof adapted to receive therethrough fasteners. The intracranial inner cup can be adapted to attach to at least one of the cranial body portion and the cranial thin edge portion, or the cranial body portion.

Still another aspect of the invention relates to surgical instruments for manipulating a craniofacial implant including a pair of pivoting jaws connected to a respective pair of finger grips, where each jaw includes spaced lobes to provide contact and preclude substantially relative movement of a craniofacial implant disposed therebetween. The surgical instrument also includes a locking mechanism disposed between the finer grips to retain the finger grips in at least one predetermined relative spacing corresponding to a nominal jaw opening. The pivoting jaw can include a pair of spaced lobes or three spaced lobes. The locking mechanism can include a ratchet system. The nominal jaw opening can have a value in the range of about 1 mm to about 10 mm when the locking mechanism is engaged. The jaws can be adapted to grasp a craniofacial implant therebetween. The nominal jaw opening can have a value in a range of about 10 mm to about 50 mm when the locking mechanism is engaged. The jaws can be adapted to clamp a craniofacial implant to bone. The pivoting jaws can be adapted to open a distance of up to about 4 mm. The distance from the lobes to the pivoting point can be up to about 70 mm. The overall instrument length can be up to about 140 mm. The pivoting jaws can be adapted to pen a distance of up to about 20 mm. The distance from the lobes to the pivoting point can be up to about 60 mm. The overall instrument length can be up to about 100 mm.

The invention also relates to a facial implant instrumentation system including various components, such as a straight periosteal elevator, a curved periosteal elevator, a cutting board with a grid system, at least one surgical instrument described above, a 1.5 mm hand drill, a sterile battery powered micro drill system allowing for a sleeve system for placement of non-sterile batteries into the battery powered micro drill, a 2.0 mm selection of screws, a screw driver, a suction drain with trocar, and an evacuation patty in various combinations. The facial implant instrumentation system includes a selection of screws, a screw driver, at least one surgical instrument described above, and at least one sterile batter powered micro drill and an evacuation patty.

BRIEF DESCRIPTION OF THE DRAWINGS

The objects and features of various aspects and embodiments of the invention can be better understood with reference to the schematic drawings described below, and the claims. The drawings are not necessarily to scale, emphasis instead generally being placed upon illustrating the principles of the invention. In the drawings, like numerals are used to indicate like parts throughout the various views.

FIG. 2A is a medial cross-sectional view of an adjustable mandible chin implant in accordance with one embodiment of the invention.

FIG. 2B is a frontal view of the adjustable mandible chin implant of FIG. 2A.

FIG. 3A is a top view of a craniofacial implant including a pair of mirror image base implant components and an optional central base segment in accordance with one embodiment of the invention.

FIG. 3B is a frontal view of the craniofacial implant of FIG. 3A.

FIG. 5A is a frontal view of an infraorbital rim implant in accordance with one embodiment of the invention.

FIG. 5B is a frontal view of the infraorbital rim implant of FIG. 5a with a different size lateral malar implant portion.

FIG. 5C is an exploded view of the infraorbital rim implant of FIG. 5A.

FIG. 5D is a lateral end view of a portion of the infraorbital rim implant of FIG. 5A.

FIG. 5E is a cross-sectional view of a portion of the infraorbital rim implant of FIG. 5A.

FIG. 8A is a lateral view of a paranasal implant with flanges in accordance with one embodiment of the invention.

FIG. 8B is a medial view of the paranasal implant of FIG. 8A.

FIG. 8C is an anterior-lateral oblique view of the paranasal implant of FIG. 8A.

FIG. 11A is a cross-sectional view of a cranial implant in accordance with one embodiment of the invention.

FIG. 11B is a cross-sectional view of the cranial implant of FIG. 11A denoting dead space.

FIG. 12A is a top perspective view of an implant positioning forceps in accordance with one embodiment of the invention.

FIG. 12B is a side view of the implant positioning forceps of FIG. 12A.

FIG. 13A is a top perspective view of an implant positioning clamp in accordance with one embodiment of the invention.

FIG. 13B is a side view of the implant positioning clamp of FIG. 13A.

FIG. 14A is a top view of an implant positioning clamp in accordance with one embodiment of the invention having multiple lobes.

FIG. 14B is a side view of the implant of FIG. 14A.

FIG. 16 is a schematic plan view of an evacuation patty in the system of FIG. 15 in accordance with one embodiment of the invention.

DETAILED DESCRIPTION OF THE INVENTION

According to various embodiments of this invention, implants can be made in multiple mating pieces to reduce the inventory of implants required, while providing a high level of customization with limited sculpting or custom shimming by the surgeon during the implant procedure. While porous polyethylene material may be used, the invention is not limited in this regard and any suitable biocompatible material may be employed (e.g., rigid or flexible, porous or nonporous, polymer or nonpolymer, etc.). The implants of the present invention may be provided in kit form with or without fasteners and/or conventional or specialized surgical instruments described herein.

Figure 1A:
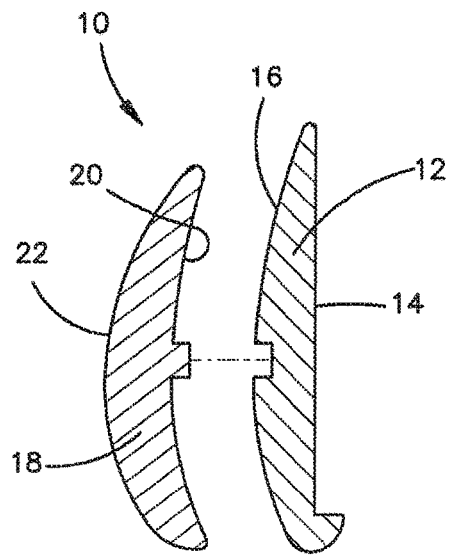
FIG. 1A is a schematic cross-sectional view of an adjustable size craniofacial implant in accordance with one embodiment of the invention.
Figure 1B:
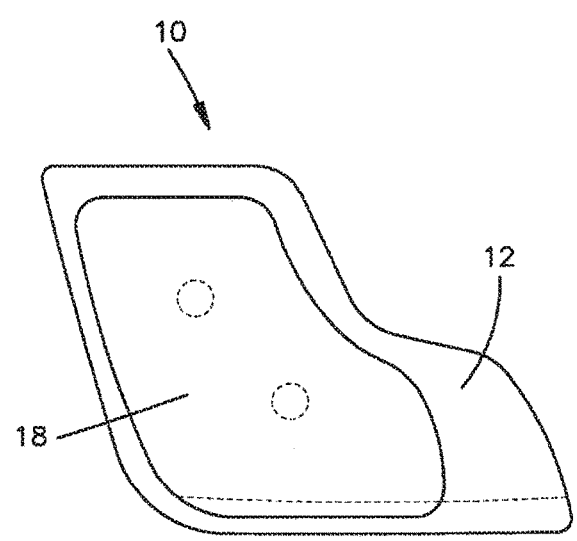
FIG. 1B is a lateral view of the adjustable size craniofacial implant of FIG. 1A.
Figure 1C:
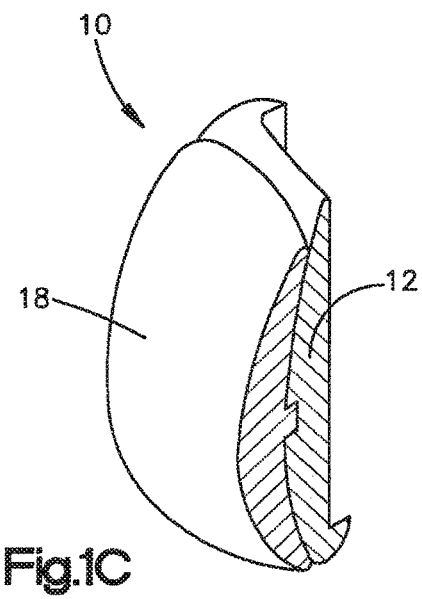
FIG. 1C is a front oblique cross-sectional view of the adjustable size craniofacial implant of FIG. 1A.

A first embodiment, an example of which is shown in FIG. 1, provides implants with adjustable projection. A two or more piece layered configuration provides controlled variability in the amount of augmentation provided by a single implant. In general, this embodiment relates to a craniofacial implant 10 including a base implant 12 having an inner base contoured surface 14 adapted to conform to a boney structure and an outer base contoured surface 16 adapted to underlie soft tissue. The craniofacial implant 10 further includes an optional onlay component 18 having an inner onlay contoured surface 20 adapted to conform to at least a portion of the outer base contoured surface 16 and an outer onlay contoured surface 22 adapted to underlie soft tissue, to adjust an overall projection of the implant. The craniofacial implant 10 further includes a means 19 to attach the onlay component 18 to the base implant 12.

In general, the craniofacial implant 10 consists of at least two pieces. The base implant 12 may be of variable shape and dimensions appropriate to augment the skeletal area of perceived deficiency. A second onlay component 18 mimics the outer shape of the base implant 12. The posterior contoured surface 20 of the onlay component 18 is congruent with the mating contoured undersurface 16 of the base implant 12. The onlay component 18 can be attached to the base implant by a press fit, connecting tabs, sutures, or other registration and interlock features known in the art. Plugs or other suitable fillers can be used to conform exposed depressions in the outermost contoured surface base implant 12 or only component 18, as necessary. Biocompatible adhesives may be used alone or in combination with the mechanical attachment schemes. The surgeon can use either the base implant 12 or the base implant 12 and the onlay component 18 together, as appropriate. Each optional third and subsequent onlay component mimics the outer shape of the underlying implant piece.

This embodiment of the invention allows for selectability in the amount of augmentation provided by a single implant, which can be useful in cases of facial asymmetry. The selectability is also useful when the surgeon is unsure initially as to the appropriate amount of augmentation. The implant with and without its onlay component can be evaluated intraoperatively. Thus, a single implant provides options in the amount of augmentation and decreases inventory requirements for the surgeon, operating facility, and implant manufacturer.

In another embodiment, an adjustable size mandible chin implant 23 (see FIG. 2A-2B) or an adjustable chin implant 27 can be provided (see FIG. 3A-3B). The configuration of the mandible base implant 24 for the mandible angle may be such that it provides up to about 6 mm or more of lateral augmentation and its optional mandible onlay component 26 provides up to about an additional 4 mm or more. Similarly, the adjustable chin implant 27 can provide up to about 5 mm or more projection base implant, with an optional mandible onlay component 26 having an additional up to about 3 mm or more projection. Additionally, due to the size of the adjustable chin implant 27, it can be made in two halves, to facilitate insertion with minimal incision size. Similar onlay components (in any number of layers) can be configured for malar, chin, and nasal dorsum implant regions.

Moreover, the adjustable chin implant 27 can optionally be configured as a three segment implant, designed to augment the contours of the chin. This embodiment of the invention, alone or in combination with the adjustable projection feature, relates to a craniofacial implant including a pair of substantially mirror image base implant components 28 and an optional central base segment 30 adapted to be disposed therebetween and connected thereto, the optional central base segment 30 selected from a group of segments having at least one different dimension, to adjust an overall dimension of the implant. The adjustable chin implant 27 further comprises means to attach the central segment to the implant components.

Conventional chin implants consist of a single piece of material of certain dimensions or two pieces joined at the center. The inclination of the lateral limbs of the implant often do not mimic the inclination of the inferior border of the mandible resulting in failure of the implant to appropriately augment the inferior border. Moreover, a fixed central width may be inappropriate for a particular patient.

Mirror image base implant components 28 of this embodiment of the invention allow the inferior border of the implant to be congruent with the inferior border of the mandible, and the central base segment 30 allows flexibility in control of the width and, therefore, shape of the chin. Thus, right and left limbs allow the inferior border of the implant to be congruent with the inferior border of any mandible. This advantageous feature of this embodiment of the invention is not possible with standard one piece implants. The central base segment 30, which can be contoured and sized to any width, allows adjustment of the width of the chin. Removable bars 32 or other structures can be used to connect the segments of the implant. The bars 32 fit into slots in each segment of the adjustable chin implant 27. The bars 32 can be attached to the mirror image base implant components 28 by a press fit, connecting tabs, sutures, or other registration and interlock features. The bars 32 may, alternatively, be integrally formed with either the central base segment 30 or with the mirror image base implant components 28. Biocompatible adhesives may be used alone or in combination with the mechanical attachment schemes.

The adjustable chin implant 27 allows greater clinical application of a single implant design. For example, a petite female requiring 5 mm of sagittal projection may be best served with a 5 mm adjustable chin implant 27 without a central base segment 30; whereas, a male requiring 5 mm of sagittal projection may be best served with a 5 mm adjustable chin implant 27 with half of the central base segment 30. Alternatively, a male requiring 5 mm of sagittal projection and a square chin may be best served with a 5 mm adjustable chin implant 27 with the entire central base segment 30. The three piece design provides controlled variability in the amount of central width provided by a single implant. Thus, the single adjustable chin implant 27 provides options in the amount of augmentation and decreases inventory requirements for the surgeon, operating facility, and implant manufacturer.

Figure 4A:
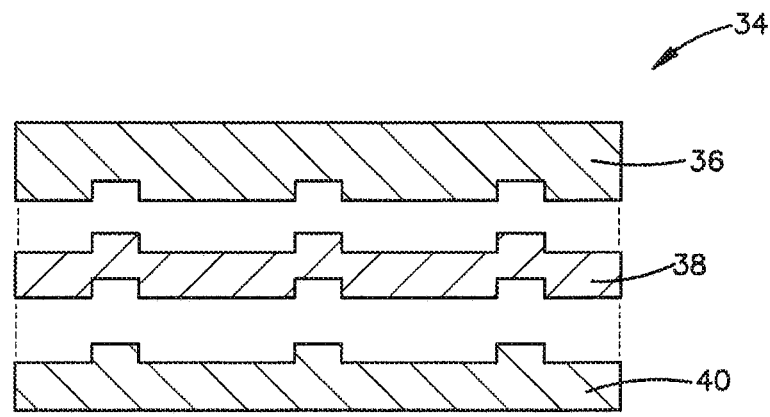
FIG. 4A is a top cross-sectional view of an adjustable elongation block implant in accordance with one embodiment of the invention.
Figure 4B:
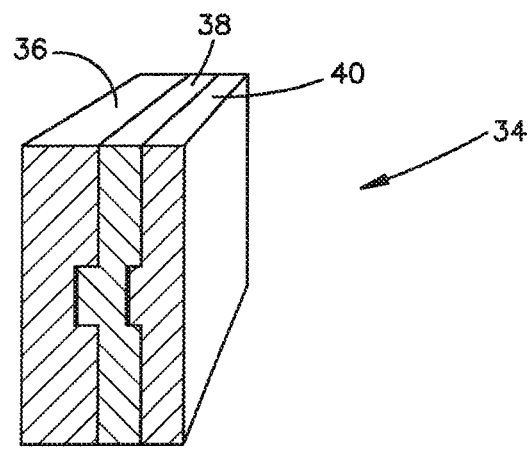
FIG. 4B is a cross-sectional side view of the adjustable elongation block implant of FIG. 4A.
Figure 4C:
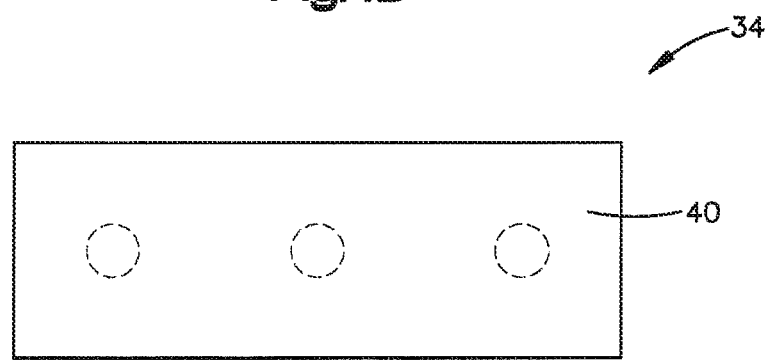
FIG. 4C is a frontal view of the adjustable elongation block implant of FIG. 4A.

Another embodiment of the invention provides an adjustable elongation block implant 34, configured to fill the space resulting from a chin osteotomy. In general, this embodiment of the invention relates to a chin osteotomy implant including a base elongation implant block 36 having an inner substantially planar surface adapted to conform to a surgically cut boney structure and an outer substantially planar opposed surface adapted to conform to at least one of an optional onlay elongation block component 38 and a mating surgically cut boney structure, and the optional onlay elongation block component 38 having an inner substantially planar surface adapted to conform to the outer surface of the base elongation implant block 36 and an outer substantially planar opposed surface adapted to conform to at least one of an optional second onlay elongation block component 40 and a surgically cut boney structure, to fill a void formed by osteotomy. The implant further includes means to attach the optional onlay elongation block component 38 to the base elongation implant block 36. One example of this embodiment is depicted in FIGS. 4A-4C.

More specifically, a horizontal osteotomy performed to vertically elongate the mandible typically leaves a gap between the mandible proper and the mobilized chin segment. This gap makes the lowered chin position unstable. The chin osteotomy adjustable elongation block implant 34 is adapted to fill this space. The adjustable elongation block implant 34 can be made of any strong material, such as a biocompatible alloplastic material. In this embodiment the adjustable elongation block implant 34 consists of a base elongation implant block 36 up to about 5 mm in height or more. Onlay elongation block components 38 of up to about 3 mm or more in height can be press fit to allow adjustment of the chin height. The adjustable elongation block implant 34 allows the space between the bone segments to be precisely controlled and maintained at these intervals. A final elongation block component 40 can cap the adjustable elongation block implant 34. The bone segments are then immobilized with the surgeon's desired fixation technique (e.g., plates and screws). The adjustable elongation block implant 34 is suitable whenever a surgeon performs a vertical elongation of the chin after horizontal osteotomy. Naturally, the onlay elongation block components 38 can be of the same or different heights and need not be rectangular in shape.

The adjustable elongation block implant 34 allows precise maintenance of the desired distance between the osteotomized segment and the mandible proper and hence, chin height. It eliminates the potential for any asymmetries at either end of the osteotomy, by filling the resultant void after osteotomy and elongation resulting instability of the movement. The adjustable elongation block implant 34 also lessens space available for hematoma accumulation and eliminates the need for bone grafts (with accompanied donor site morbidity) or use of bone substitutes that may not provide sufficient rigidity. The need to create spacers, custom-carved from for example, large polyethylene blocks, is also eliminated. The use of the elongation block implant 34 provides for more efficient, precise and predictable surgery. Further, the adjustable nature of the elongation block implant 34 allows intraoperative adjustment without penalty of opening another implant.

Another embodiment of the invention depicted in FIGS. 5A-5E, relates to an infraorbital rim implant 42, typically used to treat congenital or post-traumatic upper midface concavity, relative upper midface deficiency after Lefort I lower maxillary advancement, as well as senescent upper midface deficiency as part of facial rejuvenation procedures. The complex configuration of the infraorbital rim and limited surgical access make placement of a conventional implant tedious and adaption to the underlying skeleton difficult. This embodiment of the infraorbital rim implant 42 includes a medial rim implant portion 44 and a lateral malar implant portion 46 selected from a group of at least two malar implants having at least one different dimension, to adjust an overall dimension of the implant. The infraorbital rim implant 42 further includes means to attach the medial rim implant portion 44 to the selected lateral malar implant portion 46.

In one embodiment, the means of attaching the lateral malar implant portion 46 and medial rim implant portion 44 is a connecting extension bar 48 joining the two halves of the infraorbital rim implant 42. The extension bar allows the infraorbital rim implant 42 to be placed as two separate halves. The connecting extension bar 48 also gives the infraorbital rim implant 42 flexibility, effectively allowing the implant to hinge to better conform to the underlying skeleton. The lateral malar implant portion 46 can include a larger malar option piece 46' similar to lateral malar implant portion 46 to allow it to cover more of the malar aspect in addition to the medial rim implant portion 44. See FIG. 5B. As with the adjustable chin implant 27 described above, the connecting extension bar 48 fits into slots in each half. The connecting extension bar 48 can be attached to each half by a press fit, connecting tabs, sutures, or other registration and interlock features known in the art. The connecting extension bar 48 may, alternatively, be integrally formed with either half, for example, with titanium wire or mesh. Biocompatible adhesives may be used alone or in combination with the mechanical attachment schemes. This aspect of the invention also presents an implant kit including a consistent medial rim implant portion 44 and two or more possible lateral malar implant portions 46, along with the connecting extension bar 48.

The infraorbital rim implant 42 design facilitates implant placement and positioning. It allows the infraorbital rim implant 42 to fit flush on the underlying skeleton and the adjacent anterior malar area to be augmented in a seamless, coordinated way. This improvement eliminates the need to modify existing implants, for example by cutting into pieces to allow placement and conformability. This improvement also eliminates the need to overlay a separate malar implant over the rim implant, if the malar area also requires augmentation. This improvement prevents inaccurate reassembly of segmented implants, and difficulties associated with placement of secondary malar implants over primary rim implants.

Figure 6B:
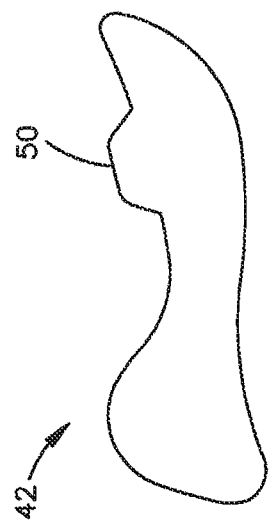
FIG. 6B is a top view of the infraorbital rim implant of FIG. 6A.
Figure 6C:
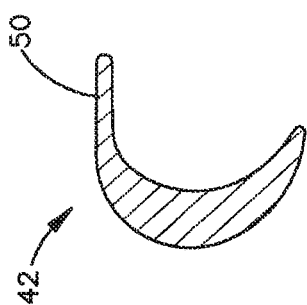
FIG. 6C is a lateral cross-sectional view of the infraorbital rim implant of FIG. 6A.
Figure 6A:
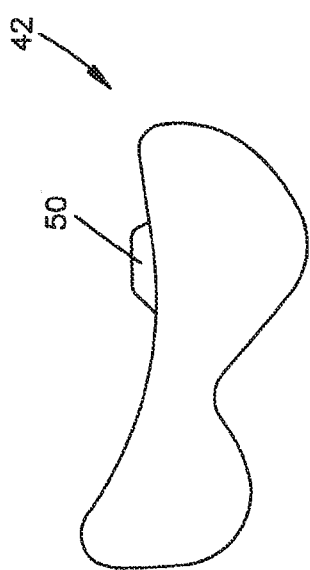
FIG. 6A is a frontal view of an infraorbital rim implant with a flange in accordance with one embodiment of the invention.
Figure 7A:
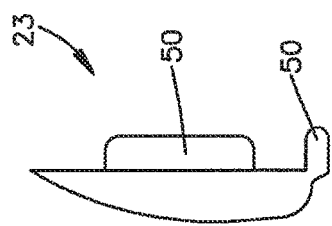
FIG. 7A is a side view of a mandible implant with flanges in accordance with one embodiment of the invention.
Figure 7C:
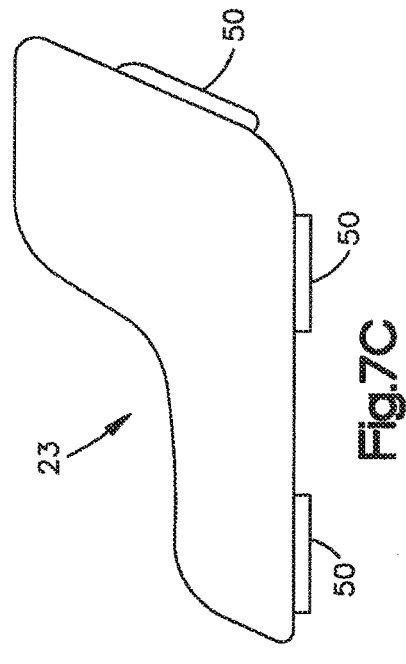
FIG. 7C is a medial view of the mandible implant of FIG. 7A.
Figure 7B:
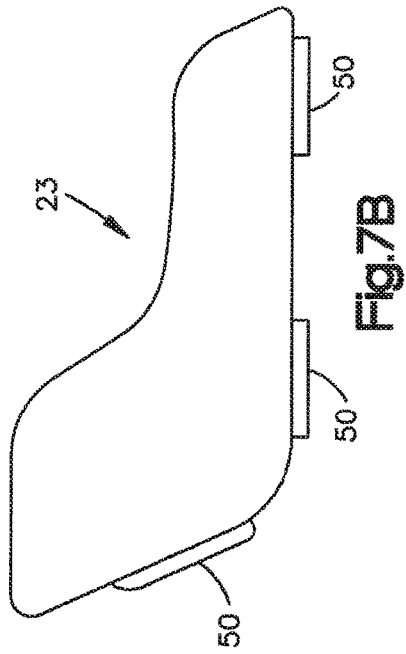
FIG. 7B is a lateral view of the mandible implant of FIG. 7A.

According to another aspect of the present invention, the implants may contain registration features that are provided to align with or abut specific features of the facial skeleton. In one embodiment, the invention relates to craniofacial implants having an inner contoured surface adapted to conform to boney structure and an outer contoured surface adapted to underlie soft tissue, and a flange 50 disposed along and extending from at least a portion of an edge thereof, the flange adapted to abut a landmark feature of the boney structure, to position initially the implant along at least one dimension. In certain embodiments, the implant can be an infraorbital rim implant 42 (see FIGS. 6A-6C), a mandible chin implant 23 (see FIGS. 7A-7C), or a paranasal implant 52 (see FIG. 8A-8C). For such embodiments, the flange 50 is positioned to abut the following respective landmark features: a lateral aspect of an orbital floor, an inferior border of a mandible body and a posterior border of a mandible ramus, and a pyriform aperture.

For example, according to a first embodiment of the invention, the placement of small flanges 50 on the posterior surface of certain facial implants (e.g., infraorbital rim, mandible and paranasal implants in the attached depictions) allows accurate positioning relative to fixed anatomic landmarks. This allows accurate, symmetric three-dimensional placement of these implants.

For such implants, the flange 50 on the infraorbital rim implant abuts the lateral aspect of the orbital floor. The series of flanges on the mandible implant abut the inferior border of the mandible body and the posterior border of the mandible ramus to provided both vertical and transverse location registration. The flanges 50 on the lateral and medial aspects of the paranasal implants abut the pyriform aperture.

The flanges 50 or projections assure accurate, symmetric implant placement and avoid reliance on visual cues to position the implants, that can lead to inaccurate positioning. The flanges 50 result in more efficient, precise and predictable outcomes.

Figure 9:
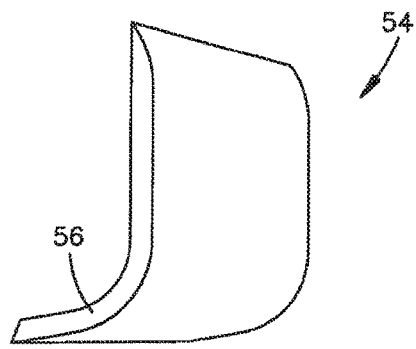
FIG. 9 is a lateral perspective view of a horizontal osteotomy implant in accordance with one embodiment of the invention.

Another embodiment of the invention relates to an implant that can be used with patients undergoing a horizontal osteotomy of the mandible that is being performed to change the location of the chin point with attached soft tissues. In this procedure, the chin point may be moved vertically sagitally, transversely, or in a combination of these directions. The osteotomy (i.e., the cut in the bone) creates a discontinuity along the inferior border of the mandible which is exaggerated by the movement of the chin segment. Depending on the amount of movement and the thickness of the overlying soft tissues, the resultant gap between the stationary mandible and its mobilized chin point may be visible and deforming. The horizontal osteotomy implant 54, depicted in FIG. 9, is adapted to bridge the gap between the two bone segments and restore a smooth mandibular border.

The horizontal osteotomy implant 54 can be placed at the time that the horizontal osteotomy is performed or at a later time. Bone at either side of the osteotomy are exposed and freed of their attached soft tissues to allow placement of the implant. The horizontal osteotomy implant 54 has a flat surface that lies on the anterior face of each bone. It has a positioning ledge 56 (e.g., a 1 mm ledge) that wraps around the inferior border of each bone. The horizontal osteotomy implant 54 is adapted to bridge the gap between the two bone segments and restore a smooth mandible border. By bridging the osteotomy gap, the contour discontinuity caused by the separation of the two bones is smoothly transitioned and any otherwise discernable appearance thereof is eliminated. A precise and stable, regular border of the mandible is restored, since the implant is tailored to fit the precise anatomic needs of the situation and can be immobilized with screws, if necessary.

Use of the horizontal osteotomy implant 54 avoids the need to inject substances (e.g., hydroxyapatite, fat, and various filler materials) percutaneously into these defects, to attempt to soften the transition between the relocated chin point and mandible. Since the horizontal osteotomy implant 54 is placed under direct vision and can be immobilized with screws, an aesthetically appealing result can be ensured.

Cranial vault implants made through computer aided design and computer aided manufacturing (CAD/CAM) are traditionally made to fill exactly a skeletal defect in the cranial vault. Its position is stabilized with plates and screws. Prominent fixation hardware may erode through the overlying scalp closure leading to implant exposure and surgical failure. Another cause of surgical failure occurs in situations when there is space between the inner surface of the implant and the brain. Such a space (termed dead space) predispose to fluid accumulation and possible infection. Two versions of a cranial vault implant are described according to various embodiments of the invention to avoid these problems.

Figure 10:
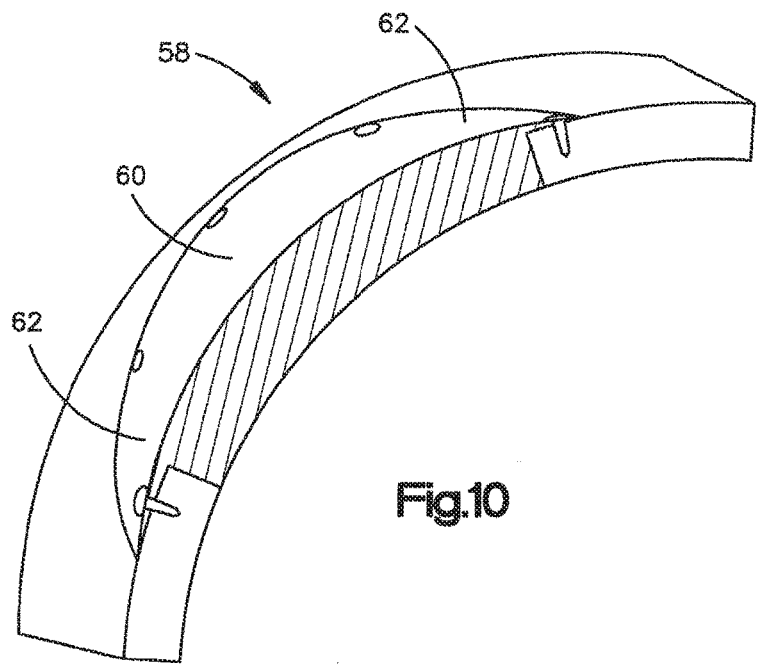
FIG. 10 is a depiction of a cranial implant in accordance with one embodiment of the invention.

In general, FIG. 10 depicts one embodiment of a cranial implant 58 that includes a cranial body portion 60 adapted to fill substantially a cranial defect and a cranial thin edge portion 62 along at least a portion of a periphery thereof. The cranial thin edge portion 62 is adapted to receive therethrough fasteners to attached the cranial implant 58 to the cranium. In one embodiment, the cranial thin edge portion 62 is a taper.

Figure 11D:
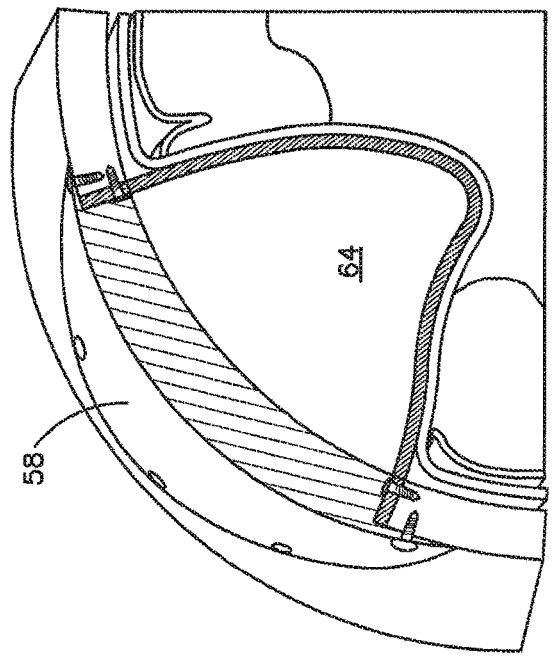
FIG. 11D is a cross-sectional view of the cranial implant of FIG. 11B with the cranial inner cup implant of FIG. 11C.
Figure 11C:
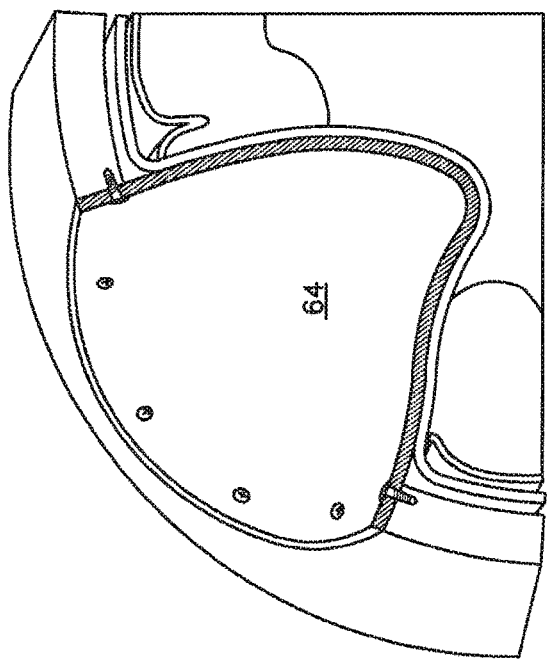
FIG. 11C is a cross-sectional view of a cranial inner cup implant filling the dead space of FIG. 11B.

In the embodiment depicted in FIG. 10 and FIG. 11A, the cranial implant 58 provides a location flange on a custom computer tomography generated cranial implant 58 that is designed to not only fill the cranial defect, but also to have the cranial thin edge portion 62 extending over the adjacent intact skull. The extension from the cranial thin edge portion 62 allows the implant to be fixed with lag screws, as opposed to higher profile plates and screws. This hardware is less prominent and less likely to erode through the overlying scalp. It also fills any gaps between the posterior surface of the scalp and any mismatch between the implant and the intact skull, that would otherwise be subject to soft tissue instability. The cranial implant 58 configuration allows the fixation hardware to be placed remote from the overlying scalp incision. It also decreases the likelihood of implant exposure, by extending the implant beyond the cranial defect and the overlying scalp incision, resulting in a more efficient, precise and predictable outcome than existing methods.

In one embodiment, the cranial thin edge portion 62 can have a thickness, tapering from up to about 1.5 mm or more to less than about 1 mm and have a lateral or radial extent of up to about 1 to 5 mm or more depending on the location of the scalp incision to the underlying area of skull reconstruction.

Another cranial implant 58 embodiment addresses situations where there is an anticipated space ("dead space") between the inner surface of the implant and the brain (see FIGS. 11A-11D). In this instance a second implant piece is employed. An intracranial inner cup 64 can be designed using magnetic resonance (MR) or computed tomography (CT) data to adapt its convex surface to the outer concave surface of the brain, thus filling the dead space. Optional perforations in the floor of the implant allow sutures to secure the dura to the outer surface of the implant thus further eliminating potential for "dead space." The intracranial inner cup 64 can be shaped to allow it to be fastened with screws to the intact edge of the skull vault. The cranial implant 58 is fashioned to restore the skull vault contour and can be adapted to fit within the perimeter edge of the intracranial inner cup 64. In certain clinical situations, both the intracranial inner cup 64 and the cranial implant 58 could be fashioned into a single implant.

Another aspect of the invention relates to surgical instruments that aid in a more efficient and precise implant surgery. The surgeon often has very limited access to the skeletal area to be augmented. Due to the aesthetics involved in craniofacial surgery, placement of facial implants often entails less exposure by incision than would otherwise be desirable for surgical access. Once access is achieved, the implant is inserted and then must be positioned and adjusted until an optimal location is achieved. Thereafter, the implant needs to be held in proper position while it is being secured to the underlying bone, typically with screws. All such access for insertion, positioning, holding, and attachment is limited, to minimize the disturbance and scarring of the patient.

According to various embodiments of the invention, implant positioning forceps 80 and implant positioning clamps 82 (see FIGS. 13A-13B) are provided to facilitate more efficient, precise, and predictable surgery than heretofore has been achievable. In general, this aspect of one embodiment of the invention relates to a surgical instrument for manipulating a craniofacial implant, the instrument 80 including a pair of pivoting jaws 72 connected to a respective pair of finger grips 74, wherein each jaw includes a pair of spaced lobes 76 to provide up to four point contact and preclude substantially relative movement of a craniofacial implant disposed therebetween. A locking mechanism 78 is disposed between the finger grips to retain the finger grips in at least one predetermined relative spacing corresponding to a nominal jaw opening 88. In various embodiments, the surgical instrument 70 has a the nominal jaw opening value in a range of up to about 1 mm to about 10 mm or more, when the locking mechanism is engaged. Such embodiments may be particularly useful as implant positioning forceps 80, wherein the jaws are adapted to grasp solely a craniofacial implant therebetween. In various alternative embodiments, the surgical instrument has a nominal jaw opening value in a range of up to about 10 mm to about 50 mm or more, when the locking mechanism 35 is engaged. Such embodiments may be particularly useful as an implant positioning clamp 82, wherein the jaws are adapted to clamp a craniofacial implant to bone.

The implant positioning forceps 80 are configured and dimensioned to securely grasp facial implants during their placement or immobilization with screws. These implant positioning forceps 80 are especially useful in the midface and upper face, where the implant cannot be clamped to the bone (which is the preferred method in the mandible). The implant positioning forceps 80 have pivoting jaws 72 that grasp the anterior surface of the implant at various regions, to hold the implant in the forceps. The pivoting jaws 72 can be non-specific, in that they need not be designed to mate with a particular implant and therefore need not have extended jaw surfaces that are designed to conform to the surfaces of a particular implant. The finger grips 74 and locking mechanism 78 permit secure, stable holding of the implant and prevent implant movement during the stabilization process.

Available conventional forceps do not open their jaws sufficiently to grasp securely most facial implants, nor do they maintain stable purchase of the implant. The pivoting jaws 72 of the forceps 80 of one embodiment of the invention have a jaw opening distance 88 of about 4 mm, a pivot arm length 84 of about 70 mm, and an overall instrument length 86 of about 140 mm. The lobes 76 provide reliable retention, without structurally damaging the implant. Other dimensions are contemplated.

In those procedures where the undersurface of the bone is accessible (e.g., the mandible), a implant positioning clamp 82 according to one embodiment of the invention may be used, an example of which is shown in FIGS. 13A-13B. The implant positioning clamp 82 holds the implant in a stable desired position relative to the bone (e.g., the mandible) so that screws can be placed to permanently immobilize the implant. In one embodiment, in which the implant is applied to the anterior surface of the mandible, one of the pivoting jaws 72 purchases the anterior face of the implant and the other jaw purchases the posterior surface of the mandible. Accordingly, the pivoting jaws 72 of the clamp grasp the anterior surface of the implant and the undersurface of the bone to which it is being secured. The pivoting jaws 72 can be non-specific, in that they need not be designed to mate with a particular implant and therefore need not have extended jaw surfaces that are designed to conform to the surfaces of a particular implant. Its finger grip 74 and locking mechanism 78 prevent implant movement during the stabilization process. The implant positioning clamp 82 configuration and dimensions allow it to immobilize temporarily an implant to the surface of the mandible so that drill holes can be made through the implant and underlying bone in anticipation of fixing the implant to the mandible with screws. The pivoting jaws 72 of the implant positioning clamp 82 of one embodiment of the invention have a jaw opening distance 88 of about 20 mm, a pivot arm length 84 of about 60 mm, and an overall instrument length 86 of about 140 mm, as depicted. This technique affords stable, essentially hands-free immobilization of the implant during its securing to the facial skeleton.

Use of these implant positioning forceps 80 and implant positioning clamps 82 permit the implant to be readily positioned and held or immobilized during the final screw stabilization process. The surgical instruments prevent misalignment of the drill holes in the implant and underlying skeleton, which must be coaxial to allow screw purchase and proper implant immobilization. Movement of the implant during the fixation process with prior art techniques results in prolonged operating times and can result in implant malposition. Use of the surgical instruments avoids implant malposition, resulting in more efficient, precise, and predictable surgery.

FIGS. 12A-12B and FIGS. 13A-13B depict a pair of twin lobed jaws; however, a single lobed jaw could be paired with a twin lobed jaw, to provide three point contact with and retention of the implant, in either the forceps or clamp configurations. At least three point contact is desired, to constrain the implant from rotation when grasped with the forceps or when held in place with the clamp. Pivoting jaws 72 with more than two lobes 76 are also contemplated. In one embodiment of such clamp 82', an example of which is depicted in FIGS. 14A-14B, one pivoting jaw 72' contains at least three lobes 76' and the other pivoting jaw contains at least two lobes 76'. The lobes 76' interdigitate when closed. This clamp 82' can be useful in clamping a chin implant to a patient's chin. The jaw opening distance 88' should be suitably sized to provide effective clamping with the ratchet or other locking mechanism 78' engaged.

Further, as depicted, the orientation of the pivoting jaw 72 opening is perpendicular to the plane of the clamp 82 and is generally aligned with the longitudinal axis of the clamp 82. Instruments with other pivoting jaw opening orientations, angularly offset jaws, curved sections between the pivot and the jaws and/or finger grips, etc. are all contemplated and considered to be within the scope of the invention. Still other embodiments can include alternatives to finger grips (e.g., pistol grips) or eliminate the grips altogether, having a tweezer configuration with a spring loaded pivot or paired cantilevered arms joined at a point remote from the jaws. The ratchet or other locking mechanism 78 could then be disposed on the jaw side of the pivot or joined section. Various embodiments of the surgical instruments can be made of surgical stainless steel or other suitable material, for reuse. Alternatively, the surgical instruments can be made of suitable polymers or composite materials that may be sterilized and included in single-use surgical kits, and disposed of once the surgical procedure has been completed.

Figure 15:
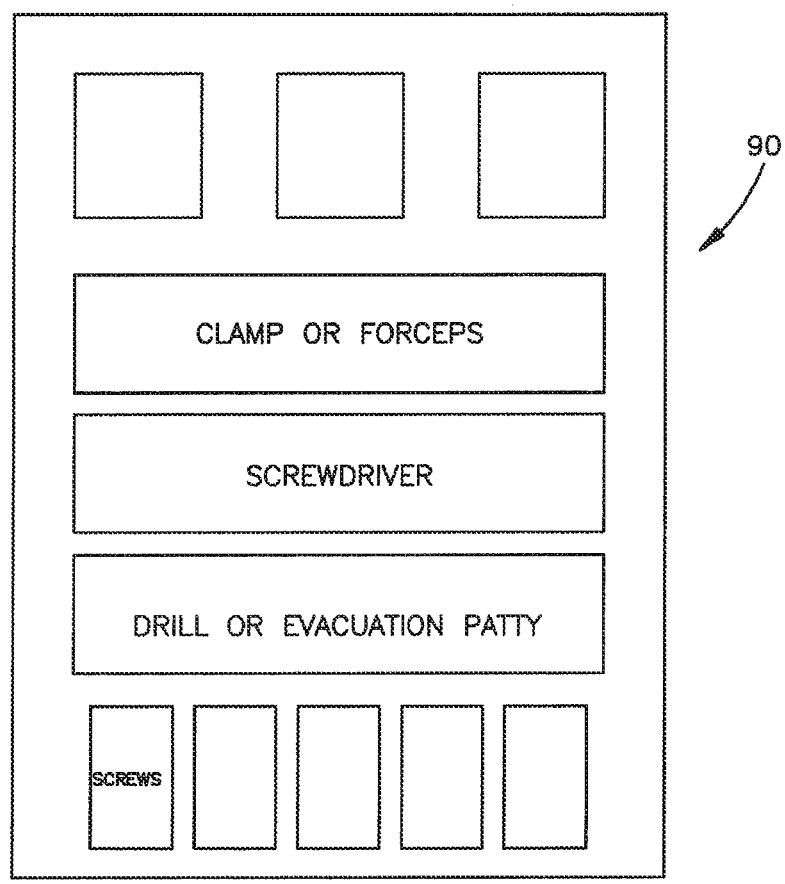
FIG. 15 is a depiction of a facial implant instrumentation system in accordance with one embodiment of the invention.

Various aspects and embodiments of the present invention include a facial implant instrumentation system 90 to facilitate accurate placement and stabilization of facial implants. An example of this embodiment is depicted in the schematic of FIG. 15. Precise and stable positioning of implants is fundamental to the success of craniofacial implant surgery. In various embodiments the facial implant instrumentation system 90 can include in various combinations some or all of the following components, including periosteal elevators, straight and curved, to develop subperiosteal pockets for implants. The facial implant instrumentation system 90 can include an implant cutting board to contour implant with a scalpel or a burr prior to implantation. The cutting board may include a grid system that allows for symmetric contouring and accurate photographic documentation of the implants used. The facial implant instrumentation system 90 can include at least one implant positioning clamp 82 and/or implant positioning forceps 80 to immobilize implants during screw fixation. The facial implant instrumentation system 90 can include a 1.5 mm hand drill and a sterile battery powered micro drill system, which has a sleeve system for placement of non-sterile batteries into an otherwise sterile drill system. The facial implant instrumentation system 90 can include a 2.0 mm or other sized selection of screws (e.g. 6 to 14 mm length), screw drivers, a suction drain with trocar, and evacuation patty 92, one embodiment of which is depicted in FIG. 16. The evacuation patty 92 can be a cottonoid 94 that is embedded a perforated catheter 96 whose other end is attached to a conventional suction source mechanism. The evacuation patty 92, an example of which is depicted in FIG. 16, is adapted to gently remove fluids and smoke from the operative field.

As described hereinabove, surgery on the facial skeleton is usually made through remote incisions. As a result the surgical field for example, the deep orbit, is visible only to the surgeon. The evacuation of blood or smoke from use of electrocautery becomes difficult. The evacuation patty 92 removes these elements from the operative field without input from an assistant or the operator. The evacuation patty 92 in one embodiment consists of a neurosurgical cottonoid 94 of dimensions of approximately about 1×1.5 cm. Imbedded in its central aspect is a perforated end of a 19 gauge plastic catheter 96. The other end of the catheter 96, which is approximately 35 cm long, is coupled to standard operating room suction tubing 98 which, in turn is connected to a suction mechanism. Placement of the small cottonoid 94 after wetting in the operative does not obscure visualization of the field. Suction applied to the wetted cottonoid 94 allows evacuation of fluids in the field through capillary action. For an example of a device used to maintain a clear field during microsurgical vessel anastomosis, see Zienowicz R J, Jupiter J B, Yaramchuk M J: A microsurgical suction mat. J. Hand Surg., 19A, 519-520 (1994), the disclosure of which is incorporated herein in its entirety.

While there have been depicted and described various embodiments, dimensions, and materials of the various embodiments and aspects of the invention, unless otherwise stated these are exemplary in nature and the scope of the invention is not limited thereto.

The invention claimed is:

1. A craniofacial implant selected from the group consisting of an infraorbital rim implant, a mandible chin implant, and a paranasal implant configured to be implanted onto a boney structure beneath soft tissue, the implant comprising:
  an inner contoured surface conforming to the boney structure when the implant is implanted onto the boney structure beneath soft tissue;
  an outer contoured surface underlying the soft tissue when the implant is implanted onto the boney structure beneath the soft tissue;
  an edge disposed about a periphery of the implant at an intersection between the inner contoured surface and the outer contoured surface; and
  at least one registration flange extending from at least a portion of the edge disposed about the periphery of the implant, wherein the registration flange is located completely along the portion of the edge, the registration flange positioned so as to abut a landmark feature of the boney structure selected from the group consisting of a lateral aspect of an orbital floor, an inferior border of a mandible body, a posterior border of a mandible ramus, and a pyriform aperture when the implant is implanted onto the boney structure beneath soft tissue such that abutment between the registration flange and the landmark feature allows accurate positioning of the implant relative to the landmark feature,
  wherein the implant defines a straight line extending from and tangent to the implant only at the edge at a first location and at the edge at a second location, the straight line intersecting with the registration flange at the first location and the registration flange extending along a direction of elongation that is substantially perpendicular to the straight line.

2. The craniofacial implant of claim 1 further comprising:
  an onlay component having an inner contoured surface adapted to conform to at least a portion of an outer contoured surface of the implant and an outer contoured surface adapted to underlie soft tissue, to adjust an overall projection of the implant.

3. The implant of claim 2, wherein the onlay component is attached to the implant.

4. The implant of claim 3, wherein the onlay component is attached to the implant by a press fit.

5. The implant of claim 3, further comprising connecting tabs attaching the onlay component to the implant.

6. The implant of claim 3, further comprising an interlocking mechanism attaching the onlay component to the implant.

7. The implant of claim 3, further comprising a registration feature attaching the onlay component to the implant.

8. The implant of claim 2, wherein at least one of the implant and the onlay component comprises a biocompatible alloplastic material.

9. The craniofacial implant of claim 1 further comprising:
  a pair of substantially mirror image implant components; and
  a central segment adapted to be disposed between the implant components and connected thereto, the central segment selected from a group of central segments each having at least one different dimension to adjust an overall dimension of the implant.

10. The implant of claim 9, wherein the central segment is attached to the implant components.

11. The implant of claim 1 comprising:
  a medial rim implant portion; and
  a lateral malar implant portion selected from at least two malar implants, the at least two malar implants having at least one different dimension, to adjust an overall dimension of the infraorbital rim implant.

12. The implant of claim 11, wherein the medial rim implant portion is attached to the selected lateral malar implant portion.

13. The implant of claim 12, further comprising a connecting extension bar attaching the medial rim implant portion to the selected lateral malar implant portion.

14. The implant of claim 11 comprising a kit comprising:
  the medial rim implant portion;
  at least two lateral malar implant portions having at least one different dimension; and
  a connecting extension bar.

15. The implant of claim 1, wherein the craniofacial implant is an infraorbital rim implant.

16. The craniofacial implant of claim 15, wherein the landmark feature comprises a lateral aspect of an orbital floor.

17. The implant of claim 1, wherein the registration flange extends along a direction offset from the inner and outer contoured surfaces prior to positioning the inner contoured surface onto the boney structure.

* * * * *